US007252995B2

United States Patent
Fu et al.

(10) Patent No.: US 7,252,995 B2
(45) Date of Patent: Aug. 7, 2007

(54) METHOD OF GENERATING NEURONS FROM STEM CELLS AND MEDIUM FOR CULTURING STEM CELLS

(76) Inventors: Yu-Show Fu, No. 155, Sec. 2, Li-Non Street, Pei Tou, Taipei (TW); Henrich Cheng, No. 322, Shih-Pai Road, Sec. 2, Pei-Tou Dist., Taipei (TW)

( * ) Notice: Subject to any disclaimer, the term of this patent is extended or adjusted under 35 U.S.C. 154(b) by 583 days.

(21) Appl. No.: 10/318,997

(22) Filed: Dec. 13, 2002

(65) Prior Publication Data
US 2004/0115806 A1 Jun. 17, 2004

(51) Int. Cl.
*C12N 5/00* (2006.01)
*C12N 5/06* (2006.01)
*C12N 5/08* (2006.01)

(52) U.S. Cl. ............... 435/377; 435/368; 435/325; 435/373; 435/404; 435/405

(58) Field of Classification Search ............... None
See application file for complete search history.

(56) References Cited
U.S. PATENT DOCUMENTS
2003/0013192 A1* 1/2003 Laeng et al. .......... 435/368

OTHER PUBLICATIONS

Sanchez-Ramos et al., Experimental Neurology 164:247-256 (2000).*
Song et al., (Nature 417:39-44, May 2, 2002).*
Rietze, R. L., et al. "Purification of a pluripotent neural stem cell from the adult mouse brain", *Nature*, (Aug. 2001), 412: 736-739.
McDonald, J. W., et al. "Transplanted embryonic stem cells survive, differentiate and promote recovery in injured rat spinal cord", *Nature Medicine*, (Dec. 1999), 5(12): 1410-1412.
Cao, Q. L., et al. "Pluripotent Stem Cells Engrafted into the Normal or Lesioned Adult Rat Spinal Cord are Restricted to a Glial Lineage", *Experimental Neurology*, (2001), 167: 48-58.
Sanchez-Ramos, J. R., et al. "Expression of Neural Markers in Human Umbilical Cord Blood", *Experimental Neurology*, (2001), 171: 109-115.
Ha, Y., et al. "Neural phenotype expression of cultured human cord blood cells in vitro", *Neuroreport*, (Nov. 2001), 12(16): 3523-3527.
Eglitis, M. A., et al. "Hematopoietic cells differentiate into both microglia and macroglia in the brains of adult mice", *Proc. Natl. Acad. Sci. USA*, (Apr. 1997), 94: 4080-4085.
Pittenger, M. F., et al. "Multilineage Potential of Adult Human Mesenchymal Stem Cells", *Science*, (Apr. 1999), 284:143-147.
Petersen, B. E., et al. "Bone Marrow as a Potential Source of Hepatic Oval Cells", *Science*, (May 1999), 284:1168-1170.
Azizi, S. A., et al. "Engraftment and migration of human bone marrow stromal cells implanted in the brains of albino rats-similarities to astrocyte grafts", *Proc. Natl. Acad. Sci. USA*, (Mar. 1998), 95: 3908-3913.
Kopen, G. C., et al. "Marrow stromal cells migrate throughout forebarin and cerebellum, and they differentiate into astrocytes after injection into neonatal mouse brains", *Proc. Natl. Acad. Sci. USA*, (Sep. 1999), 96: 10711-10716.
Woodbury, D., et al. "Adult Rat and Human Bone Marrow Stromal Cells Differentiate into Neurons", *Journal of Neuroscience Research*, (2000), 61: 364-370.

* cited by examiner

*Primary Examiner*—Brenda Brumback
*Assistant Examiner*—Daniel C Gamett
(74) *Attorney, Agent, or Firm*—Akin Gump Strauss Hauer & Feld LLP (57) ABSTRACT

The present invention relates to a method of generating neurons from stem cells which comprises culturing neurons in a medium and culturing the stem cells in the resultant mixture. The present invention also relates to a medium for culturing stem cells prepared by culturing neurons in a base culture medium.

12 Claims, 8 Drawing Sheets

0d: treated for 0 day
6d: treated for 6 days
12d: treated for 12 days
B: adult rat brain extract

0d: treated for 0 day
6d: treated for 6 days
12d: treated for 12 days
B : adult rat brain extract

METHOD OF GENERATING NEURONS FROM STEM CELLS AND MEDIUM FOR CULTURING STEM CELLS

FIELD OF THE INVENTION

The present invention relates to a method of generating neurons from stem cells and a medium for culturing stem cells.

BACKGROUND OF THE INVENTION

Many clinically common chronic neurodegenerative diseases, such as Parkinson's disease, Alzheimer's disease, Huntington's disease, and amyotrophic lateral sclerosis, are resulted from the degeneration and death of neurons in the central nervous system (CNS). Neurons, unlike epithelial and liver cells, cannot regenerate quickly. Although there are indeed stem cells present in the CNS, which can replicate and differentiate either under normal conditions or when neurons are damaged, their replication is quite slow and the proportion of neuronal differentiation is very low. Most of the stem cells in the CNS differentiate into glial cells and thus cannot rescue the neurodegenerative diseases.

Neuron transplantation has provided a direction for treating neurodegenerative diseases. Researchers have been trying to generate neurons from various stem cells both in vitro and in vivo. Stem cells are believed to possess certain characteristics, including self-renewal, pluripotency, proliferation, longevity and differentiation. Fetuses, umbilical cord blood and bone marrow are the most common sources of human stem cells for clinical applications. In fetuses, stem cells applicable in treating pathological changes of the central nervous system were mainly embryonic stem cells of blastocyst and neural stem cells (R. L. Rietze et al., 2001, *Nature* 412: 736-739). Researches have shown that after transplantation of embryonic stem cells (J. W. McDonald et al., 1999, *Nature Medicine* 5: 1410-1412) or neural stem cells (Q. L. Cao et al., 2001, *Experimental Neurology* 167: 48-58) for repairing a spinal trauma, these cells mainly differentiated into astrocytes and oligodendrocytes and only extremely few cells turned into neuronal cells. Apart from the difficulty in retrieving, the low survival rate after transplantation, and the extremely low rate for turning into neural cells, transplantation of fetus tissues is also hindered by disputes in the aspects of religion, law and ethic and therefore is not available to all.

The repair of damaged neural cells by direct implantation of haematopoietic stem cells of umbilical cord blood has yet to be studied. However, in vitro model showed that haematopoietic stem cells of umbilical cord blood cultured in 0.001% of β-mercaptoethanol (BME) could be transformed into precursors of neural cells, and then 10% of these cells could be further induced to differentiate into neural cells and glial cells (J. R. Sanchez-Ramos et al., 2001, *Experimental Neurology* 171: 109-115; and Y. Ha et al., 2001, *Neuroreport* 12(16): 3523-3527). Since the conversion rate of umbilical cord blood stem cells into neuronal cells was relatively low, the research and application of umbilical cord blood mainly focused on haematological diseases.

Bone marrow contains hematopoietic stem cells that provide a continuous source for progenitors of red cells, platelets, monocytes, granulocytes, and lymphocytes. Moreover, bone marrow also contains cells that meet the criteria for stem cells of nonhematopoietic tissues. Hematopoietic stem cells from adult bone marrow have been reported to be able to differentiate into both microglia and macroglia in the brains of mice (M. A. Eglitis et al., 1997, *Proc. Natl. Acad. Sci.* 94: 4080-4085). Nonhematopoietic stem cells from bone marrow stroma have been referred to as bone marrow stromal cells (BMSCs) or bone marrow mesenchymal cells. BMSCs are capable of differentiating into osteogenic, chondrogenic, adipogenic, myogenic and other lineages in vitro (M. F. Pittenger et al., 1999, Science 284: 143-147 and B. E. Petersen et al., 1999, Science 284: 1168-1170). Recently, BMSCs (S. A. Azizi et al., 1998, *Proc. Natl. Acad. Sci.* 95: 3908-3913; and G. C. Kopen et al., 1999, *Proc. Natl. Acad. Sci.* 96: 10711-10716) have been reported to be able to differentiate into neurons in vivo.

All the above methods of generating neurons from multipotent cells have one common problem: most of the multipotent stem cells differentiate into glial cells (astrocytes, oligodendrocytes etc.) instead of neurons. Only for in vitro culture of BMSCs, it has been observed that BME has a significant effect on neuronal differentiation, which induces about 80% of the cultured BMSCs to differentiate into neurons (D. Woodbury et al., 2000, *Journal of Neuroscience Research* 61: 364-370). However, BME is toxic for proteins and thus unsuitable for use in human bodies (K. White et al., 1973, *Journal of Pharmaceutical Sciences* 62: 237-241). Therefore, there is still a need for an efficient method to transform stem cells into neurons.

SUMMARY OF THE INVENTION

The present invention provides a method of generating neurons from stem cells which comprises culturing neurons in a medium and culturing the stem cells in the resultant mixture.

The present invention also provides a medium for culturing stem cells which is prepared by culturing neurons in a base culture medium.

BRIEF DESCRIPTION OF THE DRAWINGS

FIG. 7(A) shows the altered cell density of umbilical mesenchymal cells induced by neuron-cultured medium on the 0, $3^{rd}$, $6^{th}$ and $9^{th}$ day post-treatment (Scale bar: 100 μm); and Figure (B) shows quantitative cell density of umbilical mesenchymal cells treated with neuron-cultured medium using DAPI staining.

DETAILED DESCRIPTION OF THE INVENTION

It is surprisingly found that stem cells cultured with a medium prepared by culturing neurons in a basic culture medium for 6-9 days can differentiate into a high proportion (87%) of functional postmitotic neurons.

Not wishing to be bound by theory, it is believed that a composition of matters is released by the cultured neurons, which provides the optimal condition for stem cells to differentiate into neurons.

When used herein, the term "stem cells" refers to any undifferentiated, pluripotent or multipotent mammalian cells including, but not limited to, embryonic stem (ES) cells, embryonic germ (EG) cells, embryonic carcinoma (EC) cells, bone marrow stromal cells, bone marrow hematopoietic cells, umbilical cord blood cells and umbilical mesenchymal cells. All of the above stem cells have been reported to be able to differentiate into neurons and/or glial cells, except for umbilical mesenchymal cells. However, through the culturing method of the present invention, even umbilical mesenchymal cells can differentiate into a high proportion of functional neurons.

Accordingly, any mammalian stem cells are suitable for use in the method of the invention. Preferably, mesenchymal cells such as BMSC or umbilical mesenchymal cells are used.

The neurons used to prepare the medium of the present invention can be derived from both the peripheral nervous system and the central nervous system (CNS) of mammals. Preferably, neurons are derived form the CNS, more preferably from the brain, and most preferably from the hippocampus.

The neurons can be cultured in any conventional culture medium to obtain the medium of the invention. Culture media suitable for use as the base medium according to the present invention include, but are not limited to, Dulbecco's Modified Eagle Medium supplemented with fetal bovine serum (FBS-DMEM).

It should be acknowledged that the base medium used in the present invention may be supplemented with other additives commonly used for cell culture.

According to the present invention, neurons are cultured in the base medium in a conventional way for 3 to 6 days, preferably 5 days to produce a medium taken from culture of the neurons which can be directly used for culturing stem cells.

According to the invention, stem cells are cultured in the medium of the invention in a conventional way for 6 to 12 days before the mature neurons are harvested. Preferably, neurons are harvested on the ninth day of culturing.

After the cultured neurons have been removed, the medium of the invention can be divided into aliquots and stored for further use.

The following assays are conducted to characterize the neurons produced by the method of the present invention.

NF Immunocytochemistry

Neurofilament (NF) is the major cytoskeleton in neurons, which is responsible for adjusting the size, appearance and diameter of dendrites of neurons. Only neurons at the late developmental stage or mature neurons express NF. Immunostaining for NF is utilized to recognize neurons at the late stage.

NeuN Immunocytochemistry

Neuron-specific nuclear protein (NeuN) is a specific protein existing in the nucleus of neurons in the central nervous system of vertebrates. NeuN binds to DNA in vitro. It is known that NeuN appears earlier than NF during the development of neurons. Therefore, immunostaining for NeuN is utilized to identify neurons at the early stage of transformation.

Western Blotting for GluR5, GluR6, GluR7 and KA2

Glutamate is the major excitatory neurotransmitter in the mammalian CNS. Most neurons have glutamate receptors to receive excitatory signals. There are mainly two groups of glutamate receptors: the ionotropic type and metabotropic type. Lonotropic type receptors can be further divided by their different selective agonists into: NMDA (N-methyl-D-aspartate) receptors, AMPA (α-amino-3-hydroxy-5-methyl-4-isoxazole propionic acid) receptors, and KA (kainate) receptors. KA receptors are formed by subunits GluR5, GluR6, GluR7, KA1 and KA2. Therefore, western blotting for GluR5, GluR6, GluR7 and KA2 is utilized to confirm the ability of neurons to synthesize functional proteins.

$Ca^{2+}$-Binding Protein Immunocytochemistry $Ca^{2+}$ plays an important role in the signal transduction pathway of cells. However, most $Ca^{2+}$s do not act alone in the cell, but are bound by $Ca^{2+}$-binding proteins. $Ca^{2+}$-binding proteins can buffer the concentration of $Ca^{2+}$ in the cell and further regulate the activities of $Ca^{2+}$. There are many $Ca^{2+}$-binding proteins present in the CNS, and those with the widest distribution are parvalbumin (PV), calbindin-D28K (CB) and calretinin. Both PV and CB belong to the EF-hand type $Ca^{2+}$-binding protein family. During the development of the nervous system of embryo, PV and CB are considered as the $Ca^{2+}$-binding proteins specifically expressed by neurons. Therefore, immunostaining for PV and CB is utilized to confirm the ability of neurons to synthesize functional proteins.

BrdU and DAPI Double Labeling

DAPI (4',6-diamidino-2-phenylindole dihydrochloride) is a fluorescent dye able to cross freely through the cell and nuclear membranes and bind to the DNAs in the nucleus, and is usually used to quantify the number of cells. Moreover, during replication, cells need to synthesize an additional set of chromosomes, and will incorporate the added BrdU (bromodeoxyuridine), which is an analog of thymidine, into the synthesized chromosomes. Thus, the observation of BrdU incorporation is utilized to confirm the replication of cells. BrdU and DAPI double labeling can confirm the replication of neurons.

BrdU and NF Double Labeling

As described above, Immunostaining for NF is utilized to confirm the identity of neurons, and BrdU labeling is utilized to confirm the replication of cells. NF and BrdU double labeling can identify the replication ability of neurons.

GAD Immunocytochemistry

The synthesis of GABA, one of the neurotransmitters, from glutamic acid is catalyzed by the enzyme glutamic acid decarboxylase (GAD). Therefore, immunostaining for GAD is utilized to confirm the ability of neurons to synthesize the neurotransmitter GABA.

The neurons generated from the method of the present invention can be used in the treatment of neurodegenerative diseases, such as Parkinson's disease, Alzheimer's disease, Huntington's disease, and amyotrophic lateral sclerosis or neuronal death induced from stroke and trauma.

The present invention is further illustrated by the following examples, which should not be taken as limitations to the scope of the present invention.

EXAMPLE 1

Preparation of Human Umbilical Mesenchymal Cells

Human umbilical cords were obtained from a clinic with child delivery service, Tsai's Obstetrical Clinic (72, Sec. 1, Shi Pai Rd., Beitou, Taipei). The umbilical cords were collected by aseptic manipulation and stored in HBSS (Biochrom L201-10) under 4 for no more than 24 hours.

The umbilical cord was first soaked in 75% ethanol for 30 seconds for sanitization. The sanitized umbilical cord was placed in $Ca^{2+}/Mg^{2+}$ free buffer (CMF, Gibco 14185-052) in a germ-free laminar flow, cut lengthwise with an autoclaved tool, and from which the blood vessels and mesenchymal tissue (Wharton's jelly) were removed. The mesenchymal tissue was diced into cubes of about 0.5 $cm^3$ and centrifuged at 250×g for 5 minutes. The supernatant was removed, and the precipitate (mesenchymal tissue) washed twice by adding a proper amount of serum-free DMEM (Gibco 12100-046) and centrifuging at 250×g for 5 minutes. The mesenchymal tissue was treated with Collagase at 37° C. for 14 to 18 hours, washed, and then treated with 2.5% typsin (Gibco 15090-046) under agitation at 37° C. for 30minutes. FBS (Hyclone SH30071.03) was added to the mesenchymal tissue to quench the activity of typsin. At this time, the mesenchymal tissue has become mesenchymal cells.

The mesenchymal cells were treated with 10% FBS-DMEM to be dispersed and counted. The mesenchymal cells can now be directly used for culturing.

EXAMPLE 2

Preparation of Neuron-Cultured FBS-DMEM

The neurons used for preparing the neuron-cultured FBS-DMEM were obtained from the brain of Sprague-Dawley rats aged 7 days (the Animal Center of National Yang-Ming University, Taipei, Taiwan, ROC).

A 50-ml centrifugation tube containing 24 ml 10% FBS-DMEM was placed in a 37° C. incubator before the subsequent operation.

The rat was given 0.3 ml 10% chloride hydrate by i.p. injection. After 3 to 4 minutes, the whole body of the totally anesthetized rat was sanitized with 75% ethanol. In a germ-free laminar flow, the brain of the rat was removed and placed in CMF. The brain was at 900 rpm for 5 minutes. The supernatant was removed, and 10% FBS-DMEM was added to the precipitate (brain tissue). The brain tissue was 15 times to be into single cells. The cell dispersion was added to the 50-ml centrifugation tube prepared above, and mixed thoroughly with the FBS-DMEM inside. The mixture was added into the poly-L-lysine coated wells of a 24-well plate and cultured in the 37° C. incubator. On the nextday Arac was added to the culture to a final concentration of 2 μM.

On the fifth day of culturing, the culture medium was removed to be used for culturing umbilical mesenchymal cells.

EXAMPLE 3

Transformation of Umbilical Mesenchymal Cells into Neurons

Umbilical cells mesenchymal cells obtained in Example 1 were cultured in the neuron-cultured FBS-DMEM prepared in Example 2 or in FBS-DMEM (Control) in a 37° C. incubator. Cultured cells were collected on the 3rd, 6th, 9th and 12th days.

Figure 1:
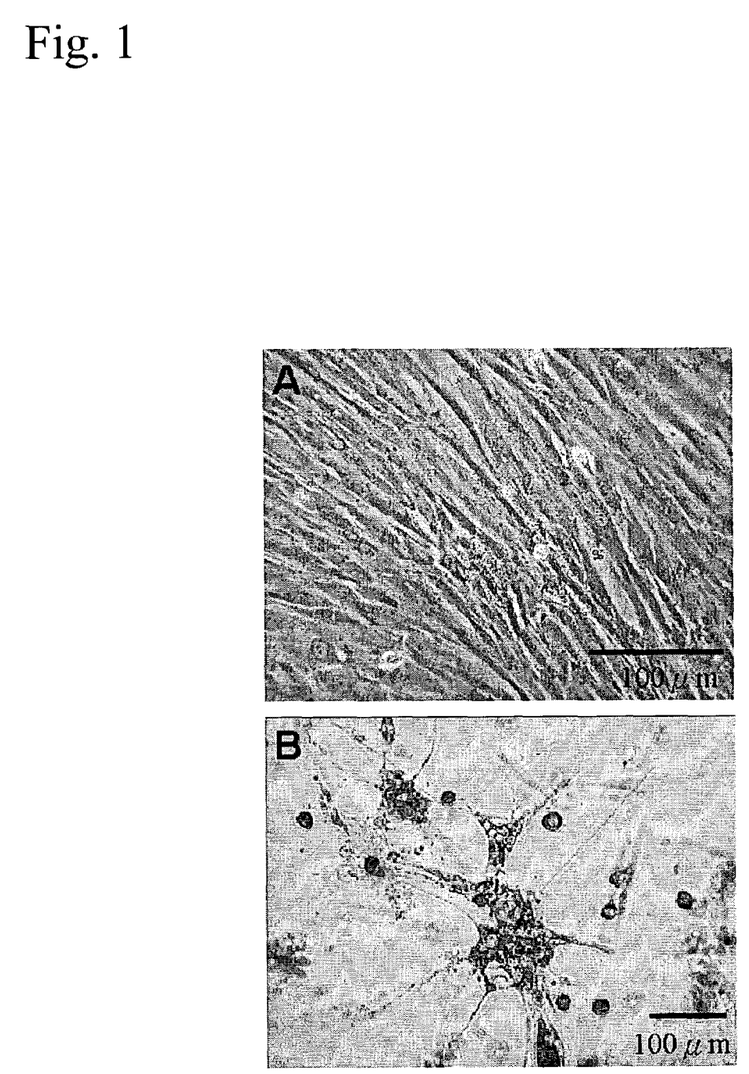
FIG. 1 shows the morphology of umbilical mesenchymal cells cultured for 6 days in (A) FBS-DMEM (Control) and (B) neuron-cultured medium.

As shown in FIG. 1(A), the morphology of umbilical mesenchymal cells culture in FBS-DMEM for 6 days (control) presented a spindle morphology and were closely attached to each other due to proliferation. Umbilical mesenchymal cells cultured in the neuron-cultured FBS-DMEM for 6 days exhibited neuronal phenotype, including cell body retraction, process elaboration, and cell cluster (FIG. 1B).

EXAMPLE 4

Assays

The cells collected in Example 3 were subjected to the following assays and their results are described below:

(I) NF Immunostaining:

Cells growing on the cover glass for 6 days were washed with 0.1 M phosphate buffer (0.1 M PBS, pH 7.4) for 5 minutes twice; fixed with the fixing solution (4% paraformaldehyde in 0.1 M PBS) for 20 minutes; washed with 0.1 M PBS for 5 minutes three times; and then treated with the blocking solution (0.05% Triton X-100, 5% normal goat serum and 3% bovine serum albumin) for 30 minutes to prevent non-specific antibody-antigen binding.

The treated cells were then reacted with primary antibodies (rabbit anti-neurofilament 200 polyclonal IgG, 1:250 diluted, Chemicon AB1982) at 4° C. for at least 12 to 18 hours; washed with 0.1 M PBS for 5 minutes three times; reacted with secondary antibodies (Biotin-conjugated goat anti-rabbit-IgG, 1:1000 diluted, Sigma b-8895) at room temperature for 1 hour; washed again with 0.1 M PBS for 5 minutes three times; reacted with avidin-biotinylated-horseradish peroxidase complex (ABC KIT, Vectorlabs PK-4000) at room temperature for 1 hour; washed with 0.1 M PBS for 5 minutes three times; and then developed with 3,3'-diaminobenzidine (5 mg DAB, 3.5 μl 30% $H_2O_2$ in 10 ml 50 mM Tris Buffer).

The obtained sample was dehydrated with ethanol of progressively increasing concentrations of 50%, 70%, 80%, 90%, 95% and 100%, as well as xylene, each for 5 minutes. The cover glass was sealed onto a slide with permount, and observed under an optical microscope (Olympus BH-2).

Figure 2:
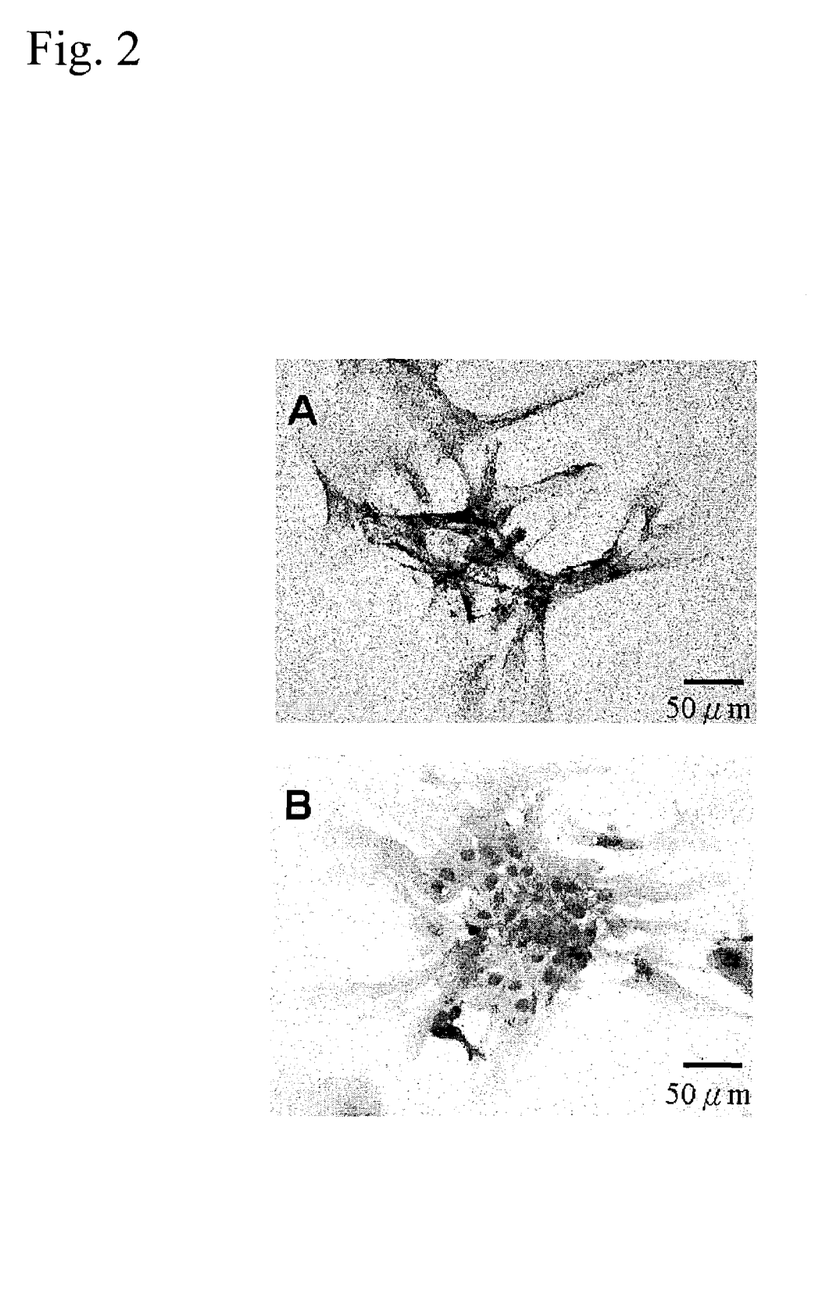
FIG. 2 shows (A) NF and (B) NeuN immunostaining of umbilical mesenchymal cells cultured in neuron-cultured medium for 6 days.

As shown in FIG. 2(A), umbilical mesenchymal cells cultured in the neuron-cultured FBS-DMEM for 6 days expressed NF, suggesting that they have been transformed into neurons.

Figure 3:
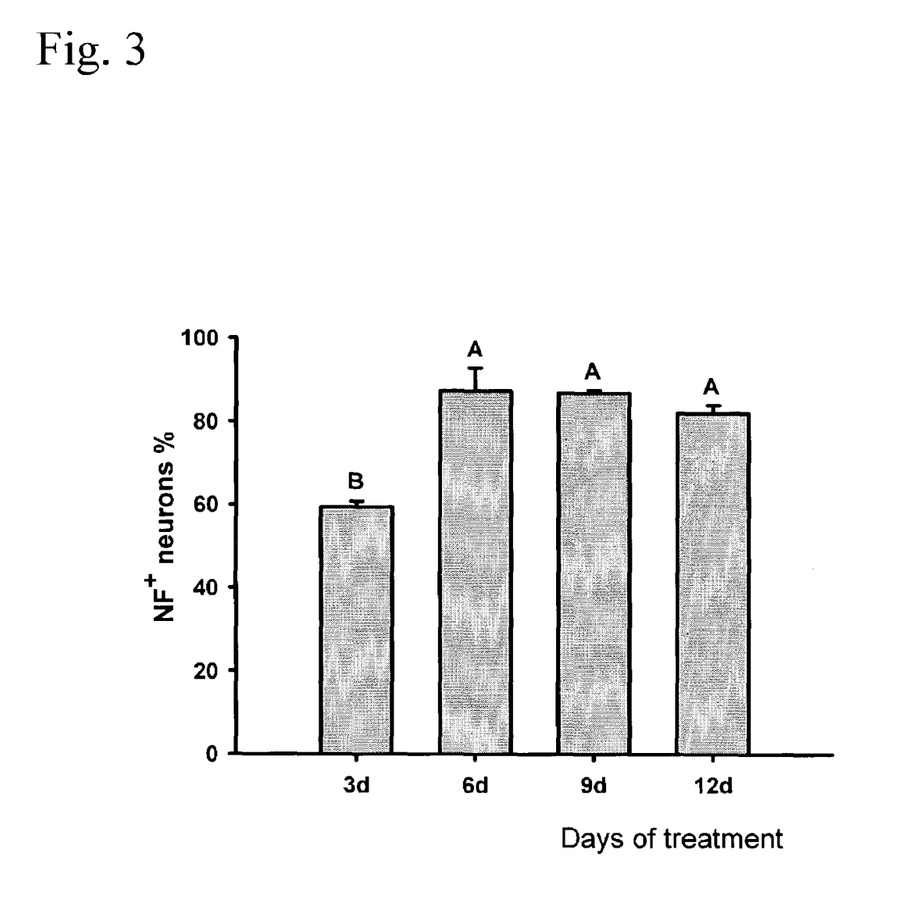
FIG. 3 shows the ratios of umbilical mesenchymal cells expressing NF after various times of treatment with neuron-cultured medium.

The ratio of umbilical mesenchymal cells expressing NF after various times of treatment with neuron-cultured FBS-DMEM was determined. As shown in FIG. 3, 59.4% of the umbilical mesenchymal cells expressed NF on the 3rd day post treatment, and the ratio of cells expressing NF reached maximum, 87.4%, on the 6th day post treatment. This ratio neither increased nor decreased along with the elongation of time (n=3, one way ANOVA followed by LSD test; P<0.01).

(II) NeuN Immunostaining:

Cells growing on the cover glass for 6 days were washed with 0.1 M phosphate buffer (0.1 M PBS, pH 7.4) for 5 minutes twice; fixed with the fixing solution (4% paraformaldehyde in 0.1 M PBS) for 20 minutes; washed with 0.1 M PBS for 5 minutes three times; and then treated with the blocking solution (0.05% Triton X-100, 5% normal goat serum and 3% bovine serum albumin) for 30 minutes to prevent non-specific antibody-antigen binding.

The treated cells were then reacted with primary antibodies (mouse anti-neuronal nuclei monoclonal IgG, 1:100 diluted, Chemicon MAB377) at 4° C. for at least 36 to 42 hours; washed with 0.1 M PBS for 5 minutes three times; reacted with secondary antibodies(Biotin-conjugated goat anti-mouse-IgG, 1:250 diluted, Chemicon AP124B) at room temperature for 1 hour; washed again with 0.1 M PBS for 5 minutes three times; reacted with avidin-biotinylated-horseradish peroxidase complex (ABC KIT, Vectorlabs PK-4000) at room temperature for 1 hour; washed with 0.1 M PBS for 5 minutes three times; and developed with 3,3'-diaminobenzidine (5 mg DAB, 3.5 µl 30% $H_2O_2$ in 10 ml 50 mM Tris Buffer).

The obtained sample was dehydrated with ethanol of progressively increasing concentrations of 50%, 70%, 80%, 90%, 95% and 100%, as well as xylene, each for 5 minutes. The cover glass was sealed onto a slide with permount, and observed under an optical microscope (Olympus BH-2).

As shown in FIG. 2(B), umbilical mesenchymal cells cultured in the neuron-cultured FBS-DMEM for 6 days expressed NeuN, suggesting that they have been transformed into neurons.

(III) Western Blotting for GluR5, GluR6, GluR7 and KA2:

(a) Preparation of Cell Membrane

Cell Membrane was prepared from umbilical mesenchymal cells treated with neuron-cultured FBS-DMEM for different times and the brain of a 7-day aged rat. Cultured cells were washed with 0.1 M phosphate buffer for 3 minutes twice. Tris-HCl buffer (50 mM, pH 7.4) was added to the cells at 4° C., and the cells were scraped off from the culture plate with a scraper. The scraped cells were put in a 15 ml Teflon-glass homogenizer, grinded twenty times to be homogenized, and then centrifuged at 30,000 g for 30 minutes at 4° C. The obtained pellet, which was mostly cell membrane, was grinded again and dissolved in a suitable volume of Tris-HCl buffer, and stored in a −20° C. refrigerator for later use.

(b) Determination of Protein Concentration

In order to be used in the western blotting assay, the concentration of proteins in each sample obtained above was determined by measuring the absorption at 595 nm. The measurement of protein concentration was conducted based on the Bradford method (M M. Bradford, 1976, Analytical Biochemistry 72: 248-254.).

(c) Electrophoresis

The proteins in the samples were separated by 20% SDS-PAGE. The separated proteins in the gel were then transferred onto a PVDF paper (NEW, NEF1002) for conducting the western blotting assay.

(d) Western Blotting

The PVDF paper containing the proteins was washed with TBS solution (0.9% NaCl in 50 mM, Tris-HCl, pH 7.4) for 30 minutes twice. Blocking was conducted with 5% skimmed milk powder dissolved in TBS buffer for 60 minutes. Then the PVDF paper was immersed in the blocking solution (0.05% Triton-X 100, 5% normal goat serum and 3% BSA) for 60 minutes, washed with TBS buffer, and reacted with primary antibodies(rabbit anti-KA2 polyclonal IgG, 1:1800 diluted, UPSTATE 06-315; goat anti-GluR5 polyconal IgG, 1:30 diluted, Santa Cruz sc-7617; goat anti-GluR6 polyclonal IgG, 1:30 diluted, Santa Cruz sc-7618; goat anti-GluR7 polyclonal IgG, 1:30 diluted, Santa Cruz sc-7620; and rabbit anti-glutamate decarboxylase polyclonal IgG, 1:1500 diluted, Chemicon AB108) at 4° C. for 12 to 18 hours.

After the reaction was completed, the PVDF paper was washed with TTBS (0.05% Tween-20 in TBS) for 30 minutes twice, immersed in the blocking solution for 60 minutes, and then reacted with secondary antibodies (Biotin-anti-goat/sheep IgG for GluR5/6/7, 1:200 diluted, Sigma B-3148; and Biotin-anti-rabbit IgG for KAR2/GAD, 1:250 diluted, Chemicon AP187B) at room temperature for 1 hour. The reacted PVDF paper was washed with TTBS for 30 minutes twice, reacted with avidin-biotinylated-horseradish peroxidase complex (ABC KIT, Vectorlabs PK-4000) at room temperature for 1 hour, washed again with TTBS for 30 minutes twice, and finally developed with DAB (5 mg DAB, 3.5 µl 30% $H_2O_2$ in 10 ml Tris-HCl, pH7.4).

Figure 4:
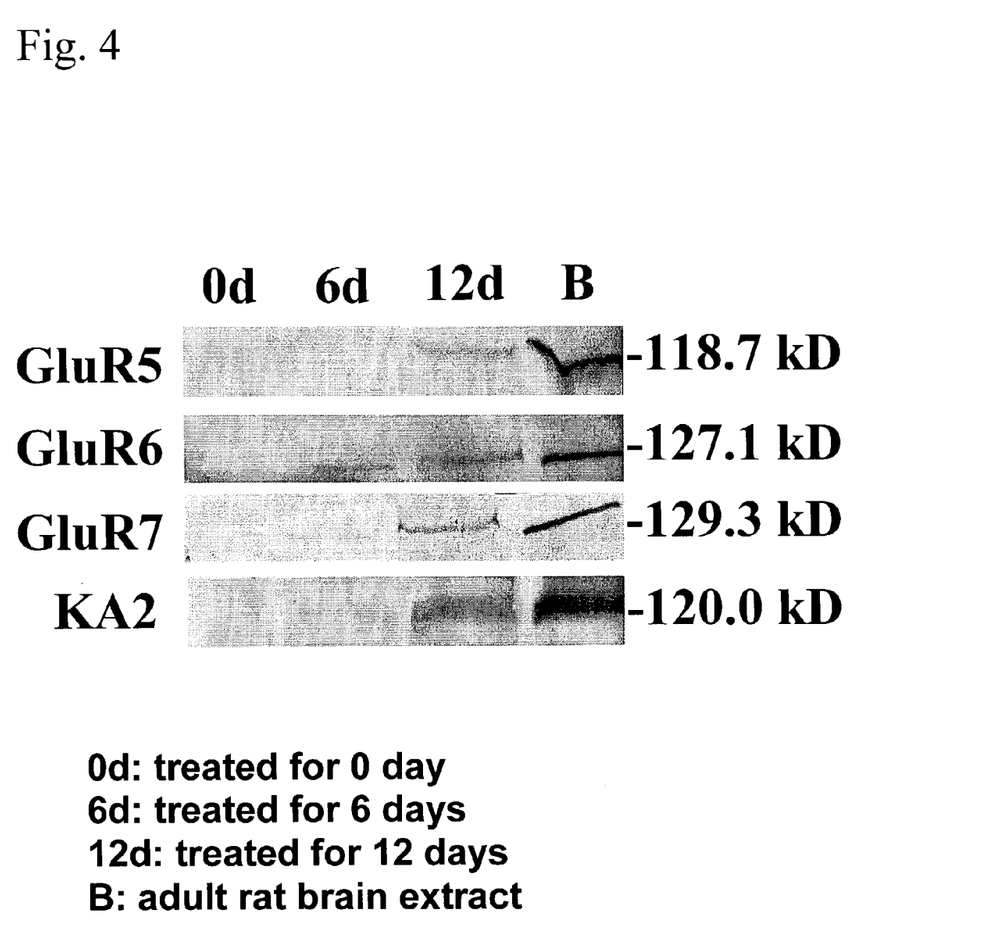
FIG. 4 shows the results of western blotting for GluR5, GluR6, GluR7 and KA2 of umbilical mesenchymal cells cultured in neuron-cultured medium.

As shown in FIG. 4, kainate receptor subunits were not expressed in umbilical mesenchymal cells before the treatment of neuron-cultured FBS-DMEM. On the 6$^{th}$ day of treatment with neuron-cultured FBS-DMEM, kainate receptor subunits, including GluR6, GluR7 and KA2, were expressed at a small quantity and GluR5, GluR6, GluR7 and KA2 were expressed significantly on the 12$^{th}$ day.

(IV) Parvalbumin (PV) and Calbindin-D28K (CB) Immunostaining:

Cells growing on the cover glass for 6 days were washed with 0.1 M phosphate buffer (0.1 M PBS, pH 7.4) for 5 minutes twice; fixed with the fixing solution (2% paraformaldehyde and 7.5% piric acid in 0.1 M PBS) for 20 minutes; washed with 0.1 M PBS for 5 minutes three times; and treated with the blocking solution (0.05% Triton X-100, 5% normal goat serum and 3% bovine serum albumin) for 30 minutes to prevent non-specific antibody-antigen binding.

The treated cells were then reacted with primary antibodies (goat anti-parvalbumin polyclonal IgG, 1:40 diluted, Santa Cruz sc-7449; and goat anti-calbindin polyclonal IgG, 1:40 diluted, Santa Cruz sc-7691) at 4° C. for at least 12 to 18 hours; washed with 0.1 M PBS for 5 minutes three times; reacted with secondary antibodies (Biotin-conjugated mouse anti-goat/sheep monoclonal diluted, IgG, 1:250 diluted, Sigma B3148) at room temperature for 1 hour; washed again with 0.1 M PBS for 5 minutes three times; reacted with avidin-biotinylated-horseradish peroxidase complex (ABC KIT, Vectorlabs PK-4000) at room temperature for 1 hour; washed with 0.1 M PBS for 5 minutes three times; and developed with 3,3'-diaminobenzidine (5 mg DAB, 3.5 µl 30% $H_2O_2$ in 10 ml Buffer).

The obtained sample was dehydrated with ethanol of progressively increasing concentrations of 50%, 70%, 80%, 90%, 95% and 100%, as well as xylene, each for 5 minutes. The cover glass was sealed onto a slide with permount, and observed under an optical microscope (Olympus BH-2).

Figure 5:
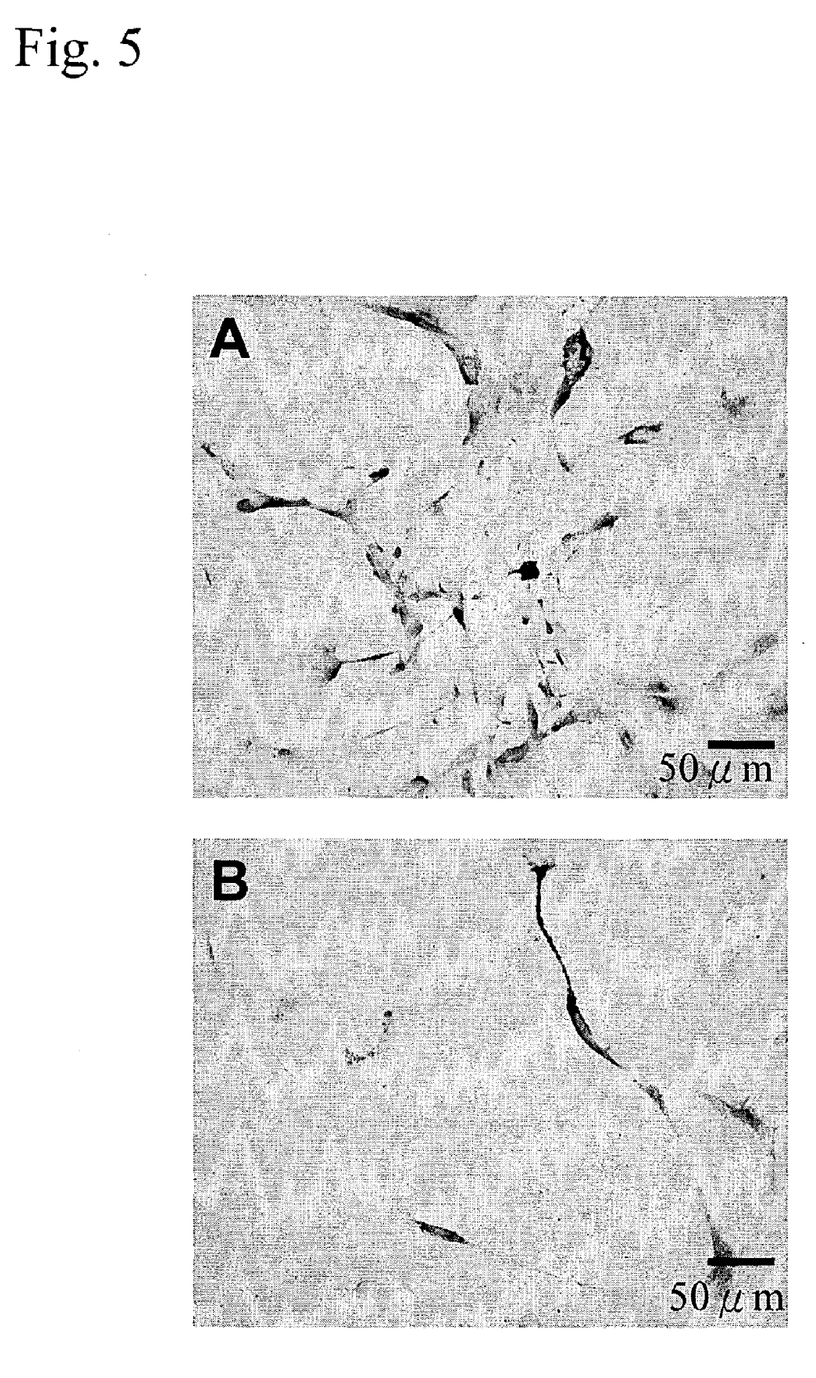
FIG. 5 shows immunostaining for (A) parvalbumin (PV) and (B) calbindin-D28K (CB) of umbilical mesenchymal cells cultured in neuron-cultured medium for 9 days.

As shown in FIG. 5, umbilical mesenchymal cells cultured in the neuron-cultured FBS-DMEM for 9 days expressed both parvalbumin (FIG. 5A) and calbindin-D28K (FIG. 5B), suggesting that they have been transformed into neurons capable of synthesizing the two $Ca^{2+}$-binding proteins.

(V) GAD Immunostaining and Western Blotting:

Cells growing on the cover glass for 6 days were washed with 0.1 M phosphate buffer (0.1 M PBS, pH 7.4) for 5 minutes twice; fixed with the fixing solution (2% paraformaldehyde and 7.5% piric acid in 0.1 M PBS) for 20 minutes; washed with 0.1 M PBS for 5 minutes three times; and treated with the blocking solution (0.05% Triton X-100, 5% normal goat serum and 3% bovine serum albumin) for 30 minutes to prevent non-specific antibody-antigen binding.

The treated cells were then reacted with primary antibodies (rabbit anti-glutamate decarboxylase polyclonal IgG, 1:1500 diluted, Chemicon AB108) at 4 for at least 12 to 18 hours; washed with 0.1 M PBS for 5 minutes three times; reacted with secondary antibodies (Biotin-conjugated goat anti-rabbit-IgG, 1:300 diluted, Sigma b-8895) at room temperature for 1 hour; washed again with 0.1 M PBS for 5 minutes three times; reacted with avidin-biotinylated-horseradish peroxidase complex (ABC KIT, Vectorlabs PK-4000) at room temperature for 1 hour; washed with 0.1 M PBS for 5 minutes three times; and developed with 3,3'-diaminobenzidine (5 mg DAB, 3.5 µl 30% $H_2O_2$ in 10 ml 50 mM Tris Buffer).

The obtained sample was dehydrated with ethanol of progressively increasing concentrations of 50%, 70%, 80%, 90%, 95% and 100%, as well as xylene, each for 5 minutes. The cover glass was sealed onto a slide with permount, and observed under an optical microscope (Olympus BH-2).

Figure 6:
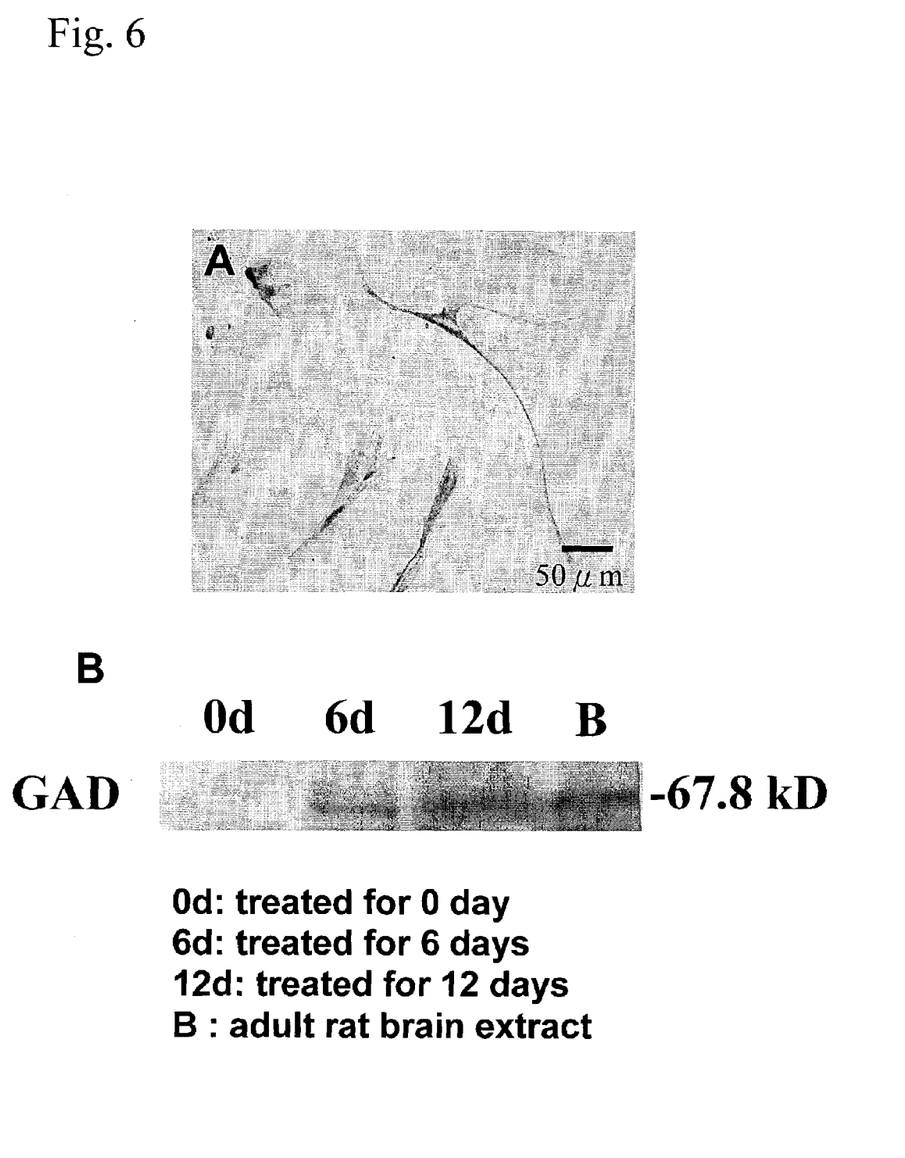
FIG. 6 shows (A) immunostaining and (B) western blotting for GAD of umbilical mesenchymal cells cultured in neuron-cultured medium for 6 days.

As shown in FIG. 6(A), umbilical mesenchymal cells cultured in the neuron-cultured FBS-DMEM for 6 days expressed GAD, suggesting that they have been transformed into neurons capable of synthesizing the neurotransmitter GABA. As shown in FIG. 6(B), the capability of umbilical mesenchymal cells to express GAD was induced on the $6^{th}$ day post-treatment and the GAD expression level was significantly increased on the $12^{th}$ day.

The results in (III), (IV) and (V) prove that the neurons derived by the method of the present invention are functional and capable of synthesizing neuron-characteristic proteins and neurotransmitters.

(VI) DAPI Staining

After treatment, the cells were washed twice with 0.1M phosphate buffer for 5 minutes each and then stained with 50 µg/ml DAPI for 30 minutes. The cells were then washed thoroughly with Tris buffer (Tris-HCl 50 mM pH=7.3) and mounted with mounting medium (Tris:glycerol=1:1) to observe and count cells under fluorescence microscope.

Figure 7:
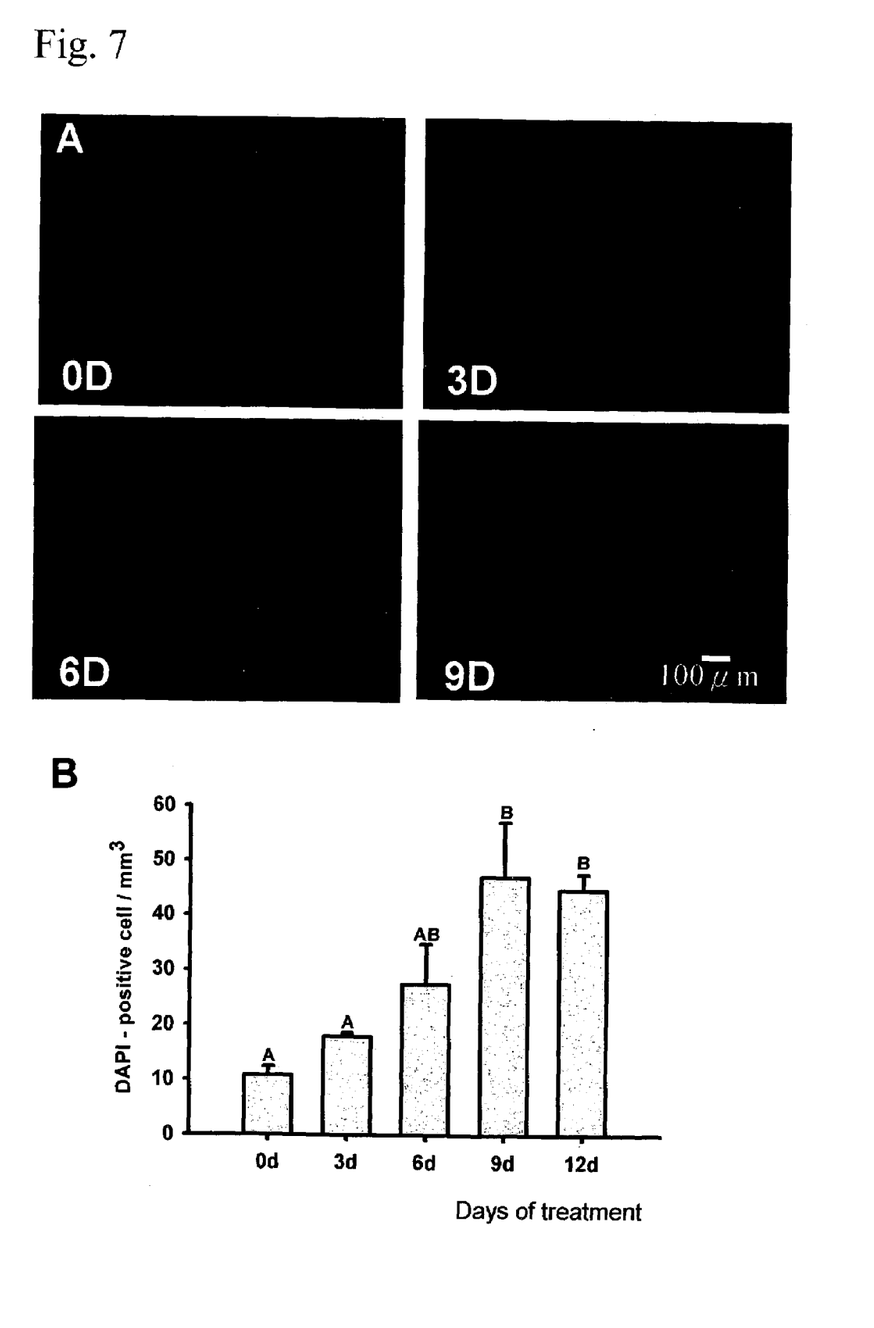

FIG. 7(A) shows photomicrographs showing the cell density. DAPI labeling (blue) was performed to determine the cell number on the 0, $3^{rd}$, $6^{th}$ and $9^{th}$ day post-treatment. FIG. 7(B) shows the cell density of umbilical mesenchymal cells after various periods of treatment in neuron-cultured FBS-DMEM. At various post treatment time points, DAPI staining was performed to determine the alternation in the cell density. The results indicated that the cell density on the 9th day post-treatment was significantly higher than that on the 3rd day (n=3, one way ANOVA followed by LSD test; $P<0.01$).

(VII) BrdU and DAPI Double Staining:

Cells growing on the cover glass were given BrdU (Sigma B-5002, prepared as a 50 mM stock solution) of a final concentration of 50 µM and allowed to grow for 24 more hours. The cells were washed with 0.1 M phosphate buffer (0.1 M PBS, pH 7.4) for 5 minutes twice; fixed with the fixing solution (70% ethanol in 50 mM glycine buffer, pH 2.0) at −20 for 30 minutes; washed with 0.1 M PBS for 5 minutes three times; and treated with the blocking solution (0.05% Triton X-100, 5% normal goat serum and 3% bovine serum albumin) for 30 minutes to prevent non-specific antibody-antigen binding.

The treated cells were then reacted with primary antibodies (mouse anti-BrdU monoclonal IgG, Chemicon MAB3222, 1:100 diluted with 0.66 mM $CaCl_2$ and 1 mM β-mercaptoethanol in 66 mM Tris buffer) at 4° C. for at least 36 to 42 hours; washed with 0.1 M PBS for 5 minutes three times; reacted with secondary antibodies (Fluorescein-conjugated goat anti-mouse-IgG, 1:50 diluted, Chemicon AP124F) and 1 mg/ml DAPI (Sigma D9542) at room temperature for 1 hour; and washed again with 0.1 M PBS for 5 minutes three times. The cover glass was attached onto a slide with mounting medium (Vector H-1000), sealed with nail-enamel and observed under a fluorescence microscope (Olympus BX50). The total cell number and BrdU-labeled cell number within unit area were counted.

(VIII) BrdU and NF Double Staining:

Cells growing on the cover glass were given BrdU (Sigma B-5002, prepared as a 50 mM stock solution) of a final concentration of 50 µM and allowed to grow for 24 more hours. The cells washed with 0.1 M phosphate buffer (0.1 M PBS, pH 7.4) for 5 minutes twice; fixed with the fixing solution (70% ethanol in 50 mM glycine buffer, pH 2.0) at −20° C. for 30 minutes; washed with 0.1 M PBS for 5 minutes three times; and treated with the solution (0.05% Triton X-100, 5% normal goat serum and 3% bovine serum albumin) for 30 minutes to prevent non-specific antibody-antigen binding.

The treated were then reacted with a primary antibody (mouse anti-BrdU monoclonal IgG, Chemicon MAB3222, 1:100 diluted with 0.66 mM $CaCl_2$ and 1 mM β-mercaptoethanol in 66 mM Tris buffer) at 4° C. for at least 12 to 18 hours; reacted with another primary antibody (rabbit anti-neurofilament polyclonal IgG, 1:250 diluted, Chemicon AB1982) at 4° C. for at least 12 to 18 hours; washed with 0.1 M PBS for 5 minutes three times; reacted with secondary antibodies (Fluorescein-conjugated goat anti-mouse-IgG, 1:50 diluted, Chemicon AP124F; Rhodamine-conjugated goat anti-rabbit-IgG, 1:50 diluted, Chemicon AP132R) at room temperature for 1 hour; and washed again with 0.1 M PBS for 5 minutes three times. The cover glass was attached onto a slide with mounting medium (Vector H-1000), sealed with nail-enamel and observed under a fluorescence microscope (Olympus BX50).

Figure 8:
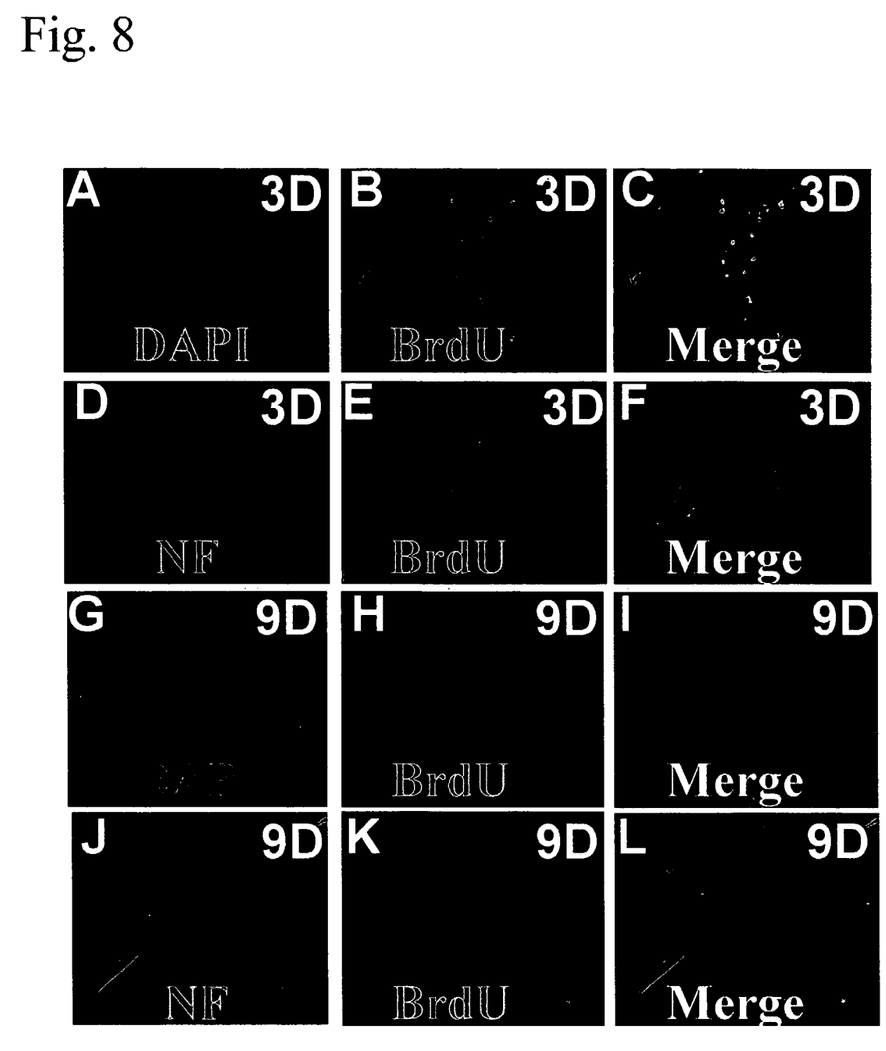
FIG. 8 shows DAPI+BrdU double staining and NF+BrdU double staining for umbilical mesenchymal cells cultured in neuron-cultured medium for 3 days (3D) and 9 days (9D).

FIG. 8 shows the results of the proliferation assay of umbilical mesenchymal cells treated with neuron-cultured 10% FBS-DMEM for 3 days (A-F). The majority of the cells labeled with DAPI (blue in A) were BrdU-positive (green in B). (C) is the merged result of (C) and (D). On the $3^{rd}$ day post treatment, these cells, although have already differentiated into cells expressing NF (red in D), were still labeled with BrdU (green in E). (F) is the merged result of (D) and (E). The cells on the $9^{th}$ day post treatment with neuron-cultured 10% FBS-DMEM lost their proliferation capability (G-L). All the cells labeled with DAPI (blue in G) were BrdU-negative (green in H). (I) is the merged result of (G) and (H). On the $9^{th}$ day post-treatment, these cells, which have differentiated into cells expressing NF (red in J), were almost not labeled with BrdU (green in K). (L) is the merged result of (J) and (K). In summary, most of the cells have been transformed into neurons and stopped proliferating on the 9th day, suggesting that the neurons on the 9th day have entered the postmitotic stage.

The results in (VII) and (VIII) demonstrate that the umbilical mesenchymal cells cultured with the neuron-cultured FBS-DMEM can proliferate and differentiate into neurons.

From the above descriptions, persons skilled in the art can easily acknowledge the essential characteristics of the present invention and, without departing from the spirit and scope thereof, can make various changes and modifications of the invention to adapt it to various usages and conditions.

The invention claimed is:

1. A method of generating neurons from stem cells which comprises: (1) culturing neurons obtained from hippocampus in a culture medium, and (2) subsequently culturing stem cells in the medium taken from the culture of the neurons, wherein the stem cells are selected from the group consisting of embryonic stem (ES) cells, embryonic germ (EG) cells, embryonic carcinoma (EC) cells, bone marrow stromal cells (BMSC), bone marrow hematopoietic cells, umbilical cord blood cells and umbilical mesenchymal stem cells.

2. The method of claim 1, wherein the neurons obtained from hippocampus are cultured in the culture medium for 3 to 6 days before culturing the stem cells in the medium taken from the culture of the neurons.

3. The method of claim 2, wherein the neurons obtained from hippocampus are cultured for 5 days.

4. The method of claim 1 wherein the stem cells are bone marrow stromal cells (BSMC) or umbilical mesenchymal cells.

5. The method of claim 1, wherein the culture medium used for culturing the neurons obtained from hippocampus is FBS-DMEM.

6. The method of claim 1, wherein the stem cells are cultured in the medium taken from culture of the neurons for 6 to 12 days.

7. The method of claim 1, further comprising the step of collecting neurons from the stem cell culture.

8. The method of claim 7, wherein the neurons are collected during the 6th to 12th day of culturing the stem cells.

9. The method of claim 7, wherein the neurons are collected during the of 6th to 9th day of culturing the stem cells.

10. A medium for culturing stem cells, which is prepared by the process of (a) culturing neurons obtained from hippocampus in a base culture medium for 3-6 days, (b) removing the neurons from the medium, and (c) storing the medium for future use for culturing stem cells.

11. The medium of claim 10, wherein the base culture medium is FBS-DMEM.

12. The medium of claim 10, wherein the neurons are cultured in the base culture medium for 5 days.

* * * * *